United States Patent [19]

Rasmussen et al.

[11] Patent Number: 4,657,922

[45] Date of Patent: Apr. 14, 1987

[54] ANXIOLYTIC 4,5-DIHYDRO-4-OXO-1H-IMIDAZOL-2-YL UREA DERIVATIVES

[75] Inventors: Chris R. Rasmussen, North Wales; Frank J. Villani, Jr., Hatfield, both of Pa.

[73] Assignee: McNeilab, Inc., Fort Washington, Pa.

[21] Appl. No.: 737,849

[22] Filed: May 24, 1985

[51] Int. Cl.$^4$ .................. A61K 31/415; C07D 233/88
[52] U.S. Cl. ..................................... 514/390; 548/311
[58] Field of Search ......................... 548/311; 514/390

[56] References Cited

U.S. PATENT DOCUMENTS 3,983,135  9/1976  Rasmussen ........................... 548/312
4,230,713  10/1980  Bare .................................. 548/309 X

OTHER PUBLICATIONS

"ASMS 32nd Annual Conference on Mass Spectrometry and Allied Topics", May 27–Jun. 1, 1984, San Antonio, Tex., p. 48, Chmeda, et al.

"American Chemical Society Division of Medicinal Chemistry", 188th ACS National Meeting, Aug. 26–31, 1984, Philadelphia, Pa., Symposium on Fluoride-Containing Materials of Medicinal Importance, Arakali, et al., Abstract No. 65.

Primary Examiner—Richard A. Schwartz
Attorney, Agent, or Firm—David J. Levy

[57] ABSTRACT

Ureas of the formula (I):

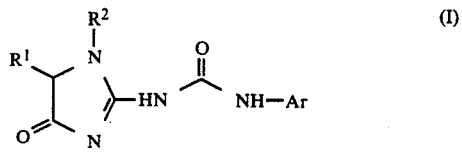

where $R^1$=alkoxy or alkylthio; $R^2$=alkyl; and Ar=-substituted or unsubstituted phenyl, useful as anxiolytic agents as well as intermediates useful in the synthesis.

19 Claims, No Drawings

ANXIOLYTIC 4,5-DIHYDRO-4-OXO-1H-IMIDAZOL-2-YL UREA DERIVATIVES

BACKGROUND OF THE INVENTION

Various imidazole urea compounds are disclosed in U.S. Pat. No. 3,983,135 as being central nervous system depressants. One of these is 1-meta-chlorophenyl-3-(1-methyl-4-oxo-2-imidazolidinylidene)urea, also known by the name N-3-chlorophenyl-N'-(4,5-dihydro-1-methyl-4-oxo-1H-imidazol-2-yl)urea or Fenobam (CAS Registry No. 63540-28-3). Also known are 1-(tetrahydro-1-alkyl-4-oxo-1H-imidazol-2-ylidene)-3-thienyl-ureas disclosed in U.S. Pat. No. 4,230,713 as anxiolytic agents.

The alkoxycreatinines 5-ethoxy-, 5methoxy-, 5-n-propoxy and 5-n-butoxycreatinine were described without any mention of biological activity, by G. B. Chheda et al. at the 32nd Annual Conference on Mass Spectrometry and Allied Topics, May 27-June 1, 1984, San Antonio, Tex., at a poster session and by A. Arakali et al. at the 188th National Meeting of the American Chemical Society, Philadelphia, Pa., Aug. 26-31, 1984 in the Division of Medicinal Chemistry presentation No. 65.

SUMMARY OF THE INVENTION

An N,N'-disubstituted urea of the formula (I):

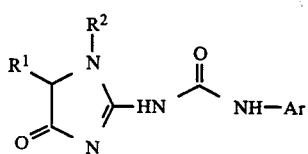

where $R^1$ is alkoxy or alkylthio, $R^2$ is alkyl and Ar is a phenyl ring, substituted or unsubstituted. The ureas are useful as anti-anxiety pharmaceutical agents. Also, aspects of the invention are intermediates and methods of use and synthesis.

DETAILED DESCRIPTION OF THE INVENTION

According to the invention, there are provided ureas of the following formula (I):

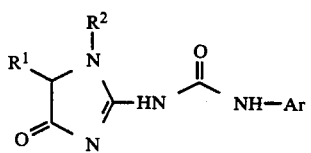

where $R^1$ is alkoxy or alkylthio, $R^2$ is alkyl and Ar is phenyl or 3-substituted phenyl wherein said substitution is selected from the group consisting of halo, trifluoromethyl, alkyl, methoxy or methylthio.

In more detail, $R^1$ is alkoxy, or alkylthio of about 1–5 carbons, including straight and branched chain moieties, such as methyl, ethyl, n-propyl, iso-propyl, n-butyl, sec-butyl, iso-butyl, tert-butyl, n-pentyl, neo-pentyl, 2- or 3-methylbutyl and 1,2-dimethylpropyl. In particular, $R^1$ is ethylthio, methoxy or tert-butoxy.

$R^2$, in more detail, is alkyl of 1–3 carbons, such as methyl, ethyl, n-propyl and iso-propyl. Preferably, $R^2$ is methyl.

Ar, in particular, is phenyl or 3-substituted phenyl wherein the substitution is halo, e.g., fluoro, chloro or bromo, $CF_3$, alkyl of 1–3 carbons such as methyl, ethyl, n-propyl and iso-propyl, methoxy or methylthio. A specific example of Ar is 3-chlorophenyl.

Also included within the scope of formula (I) ureas are solvates, such as hydrates and alcoholates, and all individual optical isomers and tautomers within formula (I). For example, tautomerization of the hydrogen on the nitrogen atom on the imidazole side of the urea is possible if the endocyclic double bond of the imidazole becomes an exocyclic double bond. The presence of an $R^1$ group other than hydrogen in the 5-position of the imidazole ring results in the possibility of optical isomers. i.e., enantiomers. Thus, when $R^1$ is either alkoxy or alkylthio of 4–5 carbons which contains an asymmetrically substituted carbon, a second optical center then exists wherein various diastereomers (2 optical centers) and enantiomers (1 optical center) may exist. The present invention includes all such isomers and isomeric mixtures.

To prepare ureas of formula (I) one starting point is the corresponding compounds of the following Formula (II) described in U.S. Pat. No. 3,983,135 for Ar=phenyl or substituted phenyl:

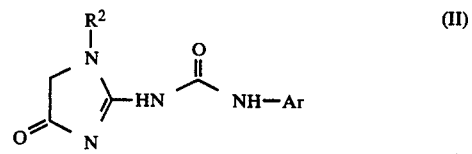

wherein $R^2$ and Ar are as defined for formula (I). From the compound of formula (II), the corresponding 5-acetyloxyurea of the following formula (III) is prepared by reaction with sodium acetate and a brominating agent, such as $Br_2$ or pyridinium hydrobromide perbromide in acetic acid at about 0°–25° C.:

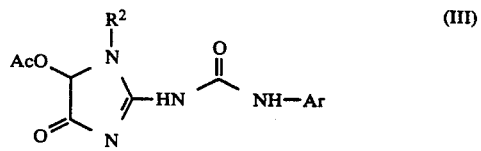

where AcO is acetoxy and $R^2$ and Ar are as defined for formula (I). The acetoxyurea (III) is then reacted e.g., as its salt with a strong acid such as HCl, with a nucleophile of the formula $R^1$—H, at a temperature of about 25° to 100° C. to obtain the urea product of formula (I). The solvent should be a polar aprotic solvent unless the nucleophile itself is also used as the solvent. Examples of polar aprotic solvents include THF, acetonitrile, dioxane, 1,2-dimethoxyethane, DMF, glyme and diglyme.

The anxiolytic activity of individual compounds of the invention may be tested in accordance with the following protocols:

Anti-Anxiety Assay (modified Geller-Seifter Conflict test)

The object of this behavioral test is to evaluate the anxiolytic potential of a test compound (see Geller and Seifter, Psychopharmacology 1:482–492, 1960). A male adult rat (250–300 g) is placed on a restricted food intake schedule. The rat is then placed in a Skinner Box and trained to press a bar in order to receive a dipperful of diluted condensed milk. When bar pressing behavior has been established, the rat is then trained on a variable interval schedule ($VI_2$), in which the rat receives a dipperful of milk on the average of once every two minutes with continued bar pressing (as opposed to receiving milk with each bar press). When the bar pressing rate has stabilized on the variable interval schedule, a punishment schedule is added. In the later situation, the animal is presented with a tone for three minutes. During this period, each bar press results in a dipperful of diluted condensed milk plus a shock (0.2 seconds). The shock level is adjusted so that the number of bar presses per punishment period does not exceed one or two. Once this behavior has stabilized, the rat is then presented with an experimental session consisting of 15 minutes on the $VI_2$ schedule followed by three minutes of the punishment schedule, repeated six times. When behavior on this final form of the test has stabilized, the rat is maintained at 80% of normal body weight (300°–330 g) by restricting his food intake. In summary, the test consists of alternating periods of unpunished milk reinforcements (milk only) and punished milk reinforcements (milk and foot shock). Under control conditions, a male rat will bar press for unpunished reinforcements and withhold responses that will be punished. Under the influence of an anxiolytic agent an animal will show a selective increase in punished responses with no significant change in the unpunished bar pressing. Significant changes in the frequency of unpunished bar pressing may be indicative of changes in the central nervous system other than an anxiolytic change (e.g., increased unpunished bar pressing may be indicative on CNS stimulation and decreased unpunished bar pressing may be indicative of CNS depression).

Dose-response studies are done on test compounds of particular interest. Compounds are usually administered by the intraperitoneal or oral route. However, the assay is appropriate for any route of administration. A number of reference anxiolytics, with proven clinical efficacy, have been assessed. In general, a clinically active anxiolytic compound produces at least a 400% increase in the median of the punished responses. The estimated dose response curve for punished responses is calculated by a "jackknife" regression analysis and the dose which would be expected to produce a 400% increase in punished responses (in an individual animal) is calculated, ED400. The estimated percent change in unpunished response at the ED400 is also calculated.

Discriminative Cue

The body weight of a male adult Sprague-Dawley rat from Charles River Laboratories is maintained at 80% of normal (normal being 300–350 g) by restricting food intake. Approximately six rats are used per group; the exact number is dependent on their ability to learn and their health during the subsequent testing. The rats are trained in accordance with the methods described in "Investigations on Drug Produced and Subjectively Experienced Discriminative Stimuli" by F. C. Colpaert, H. Lal, C. J. Niemergeers, P. A. Janssen in Life Sciences, Vol 16, pps 705–716. Before being put into the test regimen, the rats must fulfill the criterion for the acceptability: being able to differentiate between two treatments as reflected by ten consecutive F. M.'s $\leq 12$.

The F.M. is the number of responses made on either or both levers before obtaining the First (dipper of) Milk. Each rat is run once a day for 15 minutes. Generally, the rats are injected intraperitoneally, 30 minutes prior to testing, with either a discriminatory drug, saline, or a test compound. Combinations of drugs and varying time schedules and routes of administration can be used, depending on the effect desired: straight substitution for, potentiation of, or antagonism of the tool drug. Daily injections are given according to two alternating weekly schedules: saline, drug, test compound, saline, drug; or drug, saline, test compound, drug, saline.

The F.M.'s number of bar presses and body weights per day are recorded for all rats. The test compound is considered as having substituted for the discriminatory drug if the animal selects the drug lever following the injection of the test compound. The number of animals selected the drug lever is recorded, and the percentage calculated. The differences in bar presses for day 2 and day 4 (control days) to day 3 (test-compound day) is tested for statistical significance (t-test).

A test agent which will substitute or "discriminate to" a reference agent is thought to share a commonality in pharmacological effects and perhaps therapeutic potential.

With respect to the compounds of the invention, the Example 1b product has an ED400 in the anti-anxiety test of $\simeq 6$ mg/kg (i.p.) with an $\simeq 3\%$ change in unpunished responses. These values compare favorably with those found for chlordiazepoxide (ED400$\simeq 4$ with an 18% change in unpunished responses) and fenobam (ED400$\simeq 4$ with a 10% change in unpunished responses). In the discriminative cue test, the Example 2 product substituted for fenobam completely (100%) at 50 mg/kg (i.p.). Examples 3 substituted for fenobam $\simeq 36\%$ at 25 mg/kg (i.p.). These data suggest some indications of potential anti-anxiety activity similar to reference anxiolytics.

The ureas of Formula (I) are useful as anxiolytic pharmaceuticals when administered in an anxiolytic therapeutically effective amount, e.g., with a pharmaceutically acceptable diluent or carrier, to a mammal such as man. Thus, a urea of Formula (I) may be administered in a manner similar to the commercial anxiolytic Librium when used in about 1 to 10 times the dosage. In more detail, the urea (I) in an amount of about 1 to 10 mg per kg of body weight per day, which dosage may be divided into 2–4 separate administrations.

To prepare the pharmaceutical composition of this invention, one or more compounds of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Injectable suspensions may also be prepared, in which case appropriate liquid carriers, suspending agents and the like may be employed.

In the following Examples, and throughout the specification, the following abbreviations may be used: mg (milligrams); g (grams); kg (kilograms); L (liters); ml (milliliters); mmole (millimoles); mol (moles); M (molar); N (normal); mp (melting point); bp (boiling point); THF (tetrahydrofuran); DMF (dimethylformamide); p.o. (per os, orally); i.p. (intraperitoneal); min (minutes); hr (hours); and C, H, N, O, etc. (the chemical symbols for the elements). Unless otherwise indicated, all temperatures are reported in °C. (degrees centigrade).

EXAMPLE 1 a.

N-(5-Acetyloxy-4,5-dihydro-1-methyl-4-oxo-1H-imidazol-2-yl)-N'-(3-chlorophenyl)urea (Formula (III)): $R^2=CH_3$; Ar=3-chlorophenyl)

A mixture of 26.7 g (0.10 mol) of N-(3-chlorophenyl)-N'-(4,5-dihydro-1-methyl-4-oxo-1H-imidazol-2-yl)urea, as described in Example I of U.S. Pat. No. 3,983,135, 32.4 g (0.40 mol) of sodium acetate and 600 ml of glacial acetic acid was warmed until all dissolved and then chilled to 12° C. With efficient stirring, 33.0 g (0.10 mol) of pyridinium hydrobromide perbromide (97%) was added portionwise over a period of 10 min. The reaction mixture was stirred for an additional 10 min at 10°–12° C. and then diluted to 4 L with ice/water. The aqueous layer was decanted and the residue dissolved in 500 ml of ether. The separated organic layer was washed with water (3×400 ml), brine, dried ($MgSO_4$), and evaporated in vacuo to give 27.2 g (84%) of the title compound. Recrystallization from ether/hexane gave an analytical sample, mp 113°–116° C.

Elemental Analysis: For $C_{13}H_{13}ClN_4O_4$. Calculated: C, 48.08; H, 4.03; Cl, 10.92; N, 17.25. Found: C, 48.10; H, 4.05; Cl, 10.90; N, 17,22.

N-3-Chlorophenyl-N'-(5-ethylthio-4,5-dihydro-1-methyl-4-oxo-1H-imidazol-2-yl)urea (Formula (I): $R^1=SCH_2CH_3$; $R^2=CH_3$; Ar=3-chlorophenyl)

A solution of 3.00 g (9.20 mmol) of N-(5-acetyloxy-4,5-dihydro-1-methyl-4-oxo-1H-imidazol-2-yl)-N'-(3-chlorophenyl)urea, the compound of Example 1a, in 75 ml of anhydrous ether was treated with anhydrous HCl until no more precipitation occurred. The solid was filtered, washed with anhydrous ether and suspended in a mixture of 1.8 ml (25 mmol) of ethyl mercaptan and 30 ml of acetonitrile. After heating under reflux for 1 hr, the reaction mixture was evaporated in vacuo. The crystalline residue was dissolved in THF/water and extracted with ether. The combined ether layers were washed with water to pH 5–6, dried ($MgSO_4$) and evaporated in vacuo. Crystallization of the residue from methanol/water afforded 2.20 g (73%) of the title compound. Recrystallization from ether/hexane and finally ethanol/water gave an analytical sample mp 102°–104° C.

Elemental Analysis: For $C_{13}H_{15}ClN_4O_2S$. Calculated: C, 47.78; H, 4.63; N, 17.14. Found: C, 47.54; H, 4.64; N, 17.13.

EXAMPLE 2

N-3-Chlorophenyl-N'-(4,5-dihydro-5-methoxy-1-methyl-4-oxo-1H-imidazol-2-yl)urea (Formula (I): $R^1=OCH_3$; $R^2=CH_3$; Ar=3-chlorophenyl)

A solution of 10.00 g (0.031 mol) of N-(5-acetyloxy-4,5-dihydro-1-methyl-4-oxo-1H-imidazol-2-yl)-N'-(3-chlorophenyl) urea. The compound from Example 1a, in 200 ml of anhydrous ether was treated with anhydrous HCl until no more precipitation occurred. The solid was filtered, with anhydrous ether and dissolved in 200 ml of warm (70° C.) methanol. The reaction mixture was cooled to room temperature and after 1 hr filtered. Concentration of the filtrate gave additional material which was combined with the first crop, dissolved in THF/water and extracted with ether. The combined ether layers were washed with water to pH 5–6, dried ($MgSO_4$) and evaporated in vacuo. Crystallization of the residue from methanol and finally methanol/pentane (5:1) afforded 3.22 g (37%) of the title compound, mp 147°–149° C.

Elemental Analysis: For $C_{12}H_{13}ClN_4O_3$. Calculated: C, 48.58; H, 4.42; Cl, 11,95; N, 18.88. Found: C, 48.54; H, 4.42; Cl, 11.93; N, 18.86.

EXAMPLE 3

N-(3-Chlorophenyl)-N'-[5-(1,1-dimethylethoxy)-4,5-dihydro-1-methyl-4-oxo-1H-imidazol-2-yl]urea (Compound with 1,1-dimethylethanol (4:1) (Formula (I): $R^1=OC(CH_3)_3$; $R^2=CH_3$; Ar=3-chlorophenyl)

A solution of 8.00 g (0.025 mol) of N-(5-acetyloxy-4,5-dihydro-1-methyl-4-oxo-1H-imidazol-2-yl)-N'-(3-chlorophenyl) urea, the compound from Example 1a, in 200ml of anhydrous ether was treated with anhydrous HCl until no more precipitation occurred. The solid was filtered, washed with anhydrous ether, and dissolved in 400 ml of warm (70° C.) t-butyl alcohol. The reaction mixture was cooled to room temperature and after 1 hr filtered, washed with ether and air dried. The resulting solid was dissolved in THF/water and extracted with ether. The combined ether layers were washed with water to pH 5–6, dried ($MgSO_4$) and evaporated in vacuo. Crystallization of the residue from t-butyl alcohol/hexane afforded 3.60 g (41% of the title compound, mp 168°–170° C.

Elemental Analysis: For $C_{15}H_{19}ClN_4O_3 \cdot \frac{1}{4}(CH_3)_3COH$. Calculated: C, 53.78; H, 6.06; Cl, 9.92; N, 15.68. Found: C, 54.15; H, 6.31; Cl, 9.96; N, 15.77.

What is claimed is:

1. A urea of the following formula (I):

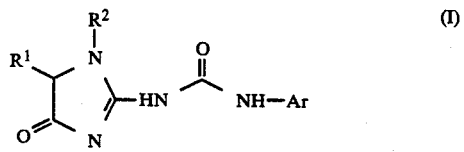

wherein
$R^1$ is alkoxy or alkylthio of about 1–5 carbons each;
$R^2$ is alkyl of 1–3 carbons; and
Ar is phenyl or 3-substituted phenyl wherein said substitution is selected from the group consisting of halo, trifluoromethyl, alkyl of 1–3 carbons, methoxy or methylthio.

2. The urea of claim 1, wherein $R^1$ is tert-butoxy.

3. The urea of claim 1, wherein said halo substitution for Ar is fluoro, chloro or bromo.

4. The urea of claim 1, wherein $R^1$ is methoxy.

5. The urea of claim 1, wherein $R^1$ is ethylthio.

6. The urea of claim 1, wherein $R^1$ is ethylthio, methoxy or tert-butoxy.

7. The urea of claim 1, wherein $R^2$ is methyl.

8. The urea of claim 1, wherein Ar is 3-substituted phenyl.

9. The urea of claim 8, wherein Ar is 3-chlorophenyl.

10. The urea of claim 1, wherein
    $R^1$ is ethylthio, methoxy or tert-butoxy;
    $R^2$ is methyl; and
    Ar is 3-substituted phenyl.

11. The urea of claim 10, wherein Ar is 3-chlorophenyl.

12. The urea of claim 1, wherein said urea is
    N-3-chlorophenyl-N'-(5-ethylthio-4,5-dihydro-1-methyl-4-oxo-1H-imidazol-2-yl)urea,
    N-3-chlorophenyl-N'-(4,5-dihydro-5-methoxy-1-methyl-4-oxo-1H-imidazol-2yl)urea, or
    N-(3-chlorophenyl)-N'-[5-(1,1-dimethylethoxy)-4,5-dihydro-1-methyl-4oxo-1H-imidazol-2-yl]urea.

13. A pharmaceutical composition for reducing anxiety comprising an anxiety reducing amount of a urea of claim 1 in association with a pharmaceutically acceptable diluent or carrier.

14. A method of relieving anxiety in a mammal which comprises administering to the mammal the pharmaceutical composition of claim 13.

15. The method of claim 14, wherein said mammal is a human.

16. An acetoxyurea of the following formula (III):

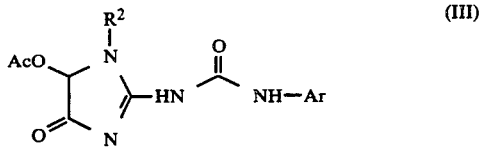

wherein
AcO is acetoxy;
$R^2$ is alkyl of 1-3 carbons; and
Ar is is phenyl or 3-substituted phenyl wherein said substitution is selected from the group consisting of halo, trifluoromethyl, alkyl of 1-3 carbons, methoxy or methylthio.

17. The acetoxyurea of claim 16, wherein $R^2$ is methyl.

18. The acetoxyurea of claim 16, wherein $R^2$ is methyl and Ar is 3-substituted phenyl.

19. The acetoxyurea of claim 18, wherein Ar is 3-chlorophenyl.

* * * * *